United States Patent [19]

Wurster

[11] 4,211,229
[45] Jul. 8, 1980

[54] LASER ENDOSCOPE

[75] Inventor: Helmut Wurster, Oberderdingen, Fed. Rep. of Germany

[73] Assignee: Richard Wolf Medical Instruments Corp., Rosemont, Ill.

[21] Appl. No.: 856,227

[22] Filed: Dec. 1, 1977

[51] Int. Cl.² ............................................. A61B 17/36
[52] U.S. Cl. ................................. 128/303.1; 128/395
[58] Field of Search ...................... 128/3, 4, 5, 6, 7, 8, 128/9, 303.1, 395, 2 R, 275.1, 303.15; 219/121 L, 121 LM; 350/54, 63

[56] References Cited

U.S. PATENT DOCUMENTS

| 2,545,865 | 3/1951 | Wallace | 128/303.15 |
|---|---|---|---|
| 2,959,089 | 11/1960 | Hett | 350/54 |
| 3,096,767 | 7/1963 | Gresser et al. | 128/303.1 |
| 3,321,265 | 5/1967 | Clave | 350/63 |
| 3,625,585 | 8/1968 | Beiser | 350/54 |
| 3,783,874 | 1/1974 | Koester | 128/395 |
| 3,796,220 | 3/1974 | Bredemeir | 128/303.1 |
| 3,821,510 | 6/1974 | Muncheryan | 128/395 |
| 3,982,541 | 9/1976 | L'Esperance, Jr. | 128/303.1 |
| 4,072,147 | 2/1978 | Hett | 128/6 |
| 4,122,853 | 10/1978 | Smith | 128/276 |
| 4,141,362 | 2/1979 | Wurster | 128/303.1 |

FOREIGN PATENT DOCUMENTS 2511131  9/1976  Fed. Rep. of Germany ........ 128/303.1

*Primary Examiner*—Robert W. Michell
*Assistant Examiner*—Arthur S. Rose
*Attorney, Agent, or Firm*—Kinzer, Plyer, Dorn & McEachran

[57] ABSTRACT

An endoscope having a sheath containing both a telescope and a laser lens system with attachments for both ranging and distancing the laser focal point and for reducing the diameter of laser beam source.

3 Claims, 3 Drawing Figures

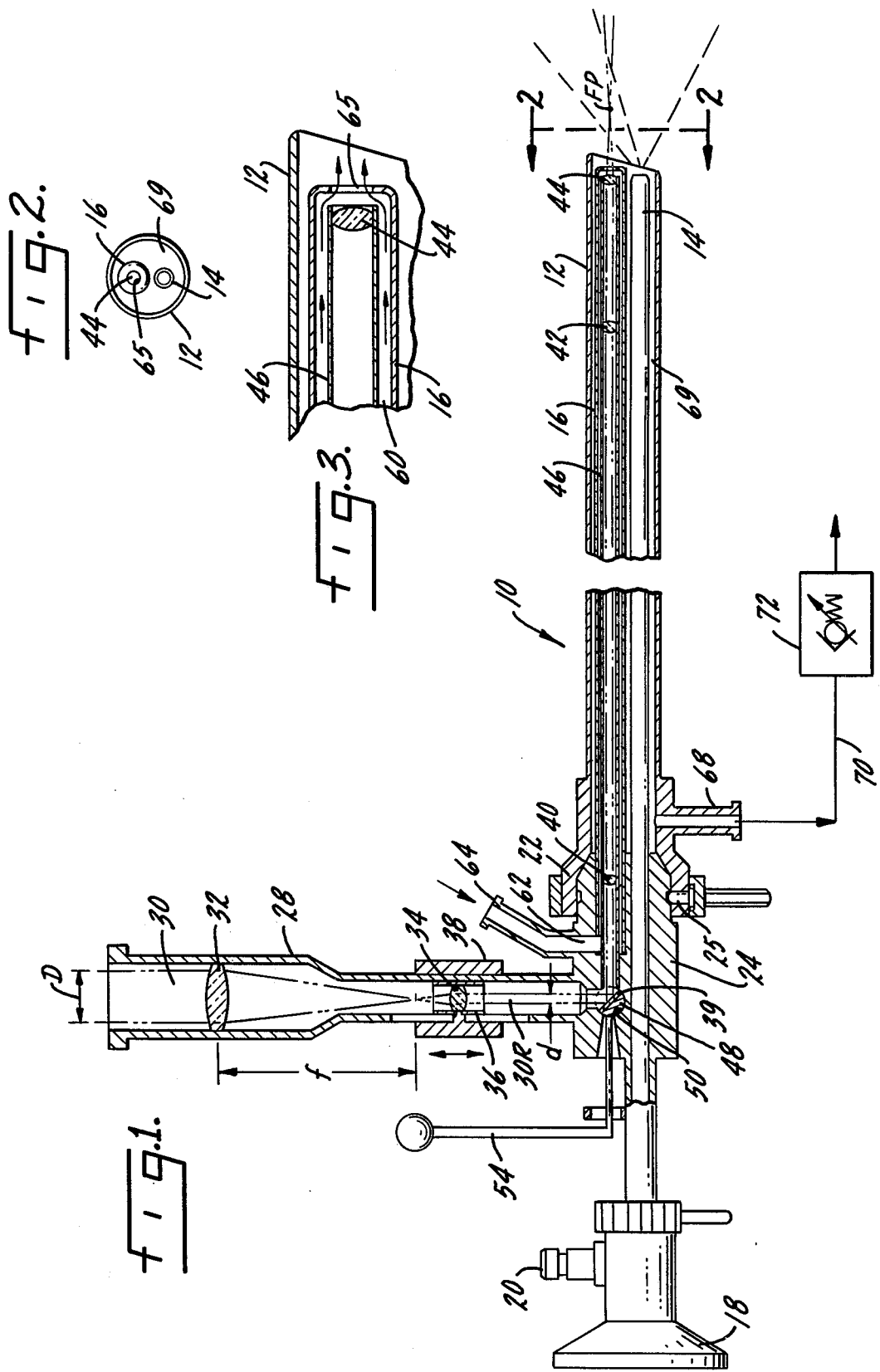

LASER ENDOSCOPE

This invention relates to a medical endoscope in which the sheath houses a telescope and a tube containing a lens relay system for a laser beam of reduced diameter, the laser beam being initially of larger diameter introduced through a sheath attachment and therein reduced to the smaller diameter.

The function of a medical endoscope is to render the interior of a body observable to the endoscopist exactly as if it were being viewed directly. The modern endoscope accomplishes this by means of a contained telescope. Specifically, the instrument may be a cystoscope, a bronochoscope, a laparascope, a rectoscope and so on, named in accordance with the specific therapy.

The typical endoscope has a long sheath containing the telescope which comprises an objective lens, an ocular or eye piece, an interposed lens relay system, and a fiber glass bundle for illumination.

The typical surgical endoscope usually contains, inside the sheath, a separate operating channel of tube form extending parallel to the telescope, into which may be inserted a surgical instrument such as a biopsy cutting forceps, an electrotome for resection, a drainage tube or whatever device is employed by the surgeon to treat the diseased or damaged tissue.

It has been mentioned to me it would be desirable for the surgeon to be able to interchange, in certain endoscope sheaths, a laser instrument and another operating instrument such as in a cystoscope or resectoscope sheath where a resecting loop (electrotome) and laser instrument could be interchanged.

The primary object of the present invention is to accomplish the desired interchange by constructing a laser lens system so it may be inserted into the operating channel of an endoscope sheath, left intact in the patient, enabling the laser to be used interchangeably with some other operating device insertable into the same channel. For example, the laser beam instrumentation may be used for urethra stricture slitting, then removed along with the telescope while leaving the sheath in place, whereafter the same telescope and a different operating instrument such as an electrotome may be inserted into the sheath for tumor resection.

In the drawing

FIG. 1 is a sectional view of an endoscope constructed in accordance with the present invention;

FIG. 2 is a detail end view taken at 2—2, FIG. 1;

FIG. 3 is a fragmentary sectional view of the distal end of the instrument, on an enlarged scale.

The endoscope 10, FIG. 1, is a cystoscope employed for transurethral endoscopic surgery, but it could be a resectoscope as well or any other endoscope ordinarily having an outer sheath 12 containing the telescope tube and assembly 14 and a tube 16 constituting the operating channel and also serving to isolate the telescope.

The surgeon customarily refers to the parts of an instrument "proximal", meaning nearest the hand or eye or "distal" meaning remote. The proximal end of the endoscope 10 is provided with an eye cup attachment 18 to which is connected an inlet 20 from a light source for illuminating a glass fiber bundle incorporated in the tube 14 between the proximal viewing lens and the distal objective lens of the telescope, not illustrated since this is known.

The tubular sheath 12 is rididly supported at its proximal end by a collar 22 which fits a male supporting member 24 which also supports both the telescope tube 14 and the tube 16 which are press fitted thereto. Collar 22 is securely detachably to support 24 as by a set screw 25.

A tubular housing 28 for the focusing section of the output laser beam 30 (derived from a laser medium, not shown) extends laterally from the supporting member 24. The laser beam output has a large diameter D, say nine mm., and in order that this diameter may be reduced to one which can be accomodated in the operating channel presented by tube 16, the laser beam 30 is collected by a lens 32 having a fixed position (focal length f) inside housing 28. The divergent laser beam, diverging beyond the focal point of lens 32, is re-paralleled (in the position substantially as shown where the distance between the focal point of lens 32 and lens 34 equals the focal length of lens 34) by an adjustable collimating lens 34 which also reduces the diameter of the laser beam to a diameter d, say two to three mm. The lens 34 is supported in a sleeve 36, slidably guided for axial movement inside the housing 28, by means of an adjusting sleeve 38 coupled to the lens supporting sleeve 36.

To guide the laser beam, now of reduced diameter (30R) down the operating channel, parallel to the observation optics, a deflecting mirror 39 is interposed in the path of beam 30R where the axis of housing 28 intercepts the axis of tube 16. Beam 30R, after deflection, is transmitted to the distal end of the instrument by a relay lens system consisting of the three lenses shown (40, 42, 44) fixed in a sleeve 46 which fits freely inside tube 16.

Lens 44 focuses the laser beam at focal point FP to perform the desired surgery but in order that the focal point may be scanned laterally over the body tissue (being subjected to stricture slitting for example) the mirror 39 is tiltable in any direction. To accomplish this, mirror 39 is presented by a semi-spherical ball-type mirror holder 48, inserted in a spherical socket 50 in support 24. Ball 48 is connected to a right-angle arm 54 which can be manipulated by the fingers so the ball may be turned universally in any direction by the surgeon.

To axially extend or retract the laser focal point FP, thereby to cut or slice in depth, lens 34 is accordingly moved axially by the focus adjustment sleeve 38. Thus it is possible not only to selectively penetrate deeper into the tissue but also to penetrate a larger area at the surface of the tissue and to coagulate a larger area as well.

To both cool and sweep clean the laser beam objective lens 44, means are provided to pass a fluid in front of lens 44. Thus, sleeve 46 is of appreciably less diameter than the retaining tube 16 to afford a passage 60 there between and this passage communicates with an opening 62 in support member 24 which is equipped with an inlet 64 for a gas ($CO_2$ for example) which, exiting through an opening 65 at the distal end of tube 16, exerts both a cooling and cleansing effect.

The same source of gas may be used to maintain bladder pressure, thereby to distend the bladder, during transurethral therapy. The internal pressure may be regulated by equipping the collar 22 with an outlet 68 communicating with the space 69 between the sheath 12 and the telescope tube 14 through which the gas may exit. Outlet 68 may be provided with a conduit 70 having a very sensitive settable pressure relief valve 72 to maintain pressure in the bladder constant during the medical procedure.

By loosening set screw 25, support member 24 together with the laser system and telescope may be withdrawn from collar 22, leaving the sheath 12 intact in the patient. Then, the telescope may be separated and it, together with another operating instrument may be assembled in a common support mating with collar 22 and inserted into the sheath.

I claim:

1. In an endoscope having an elongated outer sheath which houses an observation telescope for observing internal body tissue at a site where surgery is being performed, said sheath having a distal end and a proximal end, a housing offset from and extending laterally of the axis of the sheath and capable of conducting a laser beam therethrough, said housing containing a first large diameter laser beam collecting lens for receiving and transmitting a laser beam therethrough, said housing also containing a second lens of considerably smaller diameter than said first lens positioned such that it receives the laser beam directly from said collecting lens and being of a shape such that it reduces the diameter of the laser beam to a fraction of its original diameter, a tube in the sheath extending parallel to the telescope, said tube containing a laser lens relay system and a laser objective lens at the distal end of the tube for concentrating the laser beam at a working focal point on the body tissue, said tube being attached to said housing, a deflecting mirror in said housing adjacent the proximal end of said tube and located on the side of the lens relay system opposite the laser objective lens in position to intercept the reduced diameter laser beam and redirect it to the laser lens relay system, said tube and housing being so oriented that the laser beam conducted by the housing will impinge on the mirror and be deflected by the mirror to the laser lens relay system, the deflecting mirror being tiltable universally in any direction whereby the laser beam may be caused to laterally scan the body tissue along any axis, said second lens being supported for axial adjusting movement along the axis of the laser beam relative to said mirror and said first collecting lens to vary axially the working focal point of the laser beam, said sheath at its proximal end being separably fitted to said housing, and means between said sheath and housing to permit coupling and uncoupling of the housing and sheath so that by uncoupling the housing and sheath said housing together with said tube attached thereto may be detached from the sheath and said tube removed along the housing to permit another instrument to be inserted into the sheath.

2. Endoscope according to claim 1 in which the laser lens relay system tube is itself contained in a separate sleeve.

3. Endoscope according to claim 2 in which there is space between said tube and the laser lens sleeve to allow gas flow therein, the gas exiting in front of the laser objective lens.

* * * * *